United States Patent [19]

Strax

[11] 4,104,528
[45] Aug. 1, 1978

[54] AUTOMATED MAMMOGRAPHY APPARATUS FOR MASS SCREENING

[75] Inventor: Norman Strax, Fredericton, Canada

[73] Assignee: Charles & Stella Guttman Breast Diagnostic Institute, New York, N.Y.

[21] Appl. No.: 733,478

[22] Filed: Oct. 18, 1976

[51] Int. Cl.² .......................... G21K 5/08; G11B 1/00
[52] U.S. Cl. ................................... 250/451; 250/469; 250/476
[58] Field of Search ............... 250/469, 451, 456, 322, 250/476

[56] References Cited
U.S. PATENT DOCUMENTS 3,569,700  3/1971  Quinn .................................. 250/469

Primary Examiner—Alfred E. Smith
Assistant Examiner—T. N. Grigsby
Attorney, Agent, or Firm—Darby & Darby

[57] ABSTRACT

Apparatus for X-raying the breasts of women wherein the X-ray images are sequentially recorded on a continuous roll of film which is advanced between X-ray exposures by an amount dependent on breast size from a supply spool to a take-up spool and which is pressed against a phosphor X-ray intensifying screen during exposures by a vacuum-actuated pressure plate. Provision is included for X-raying a large breast in portions without subjecting any single portion of the breast to X-radiation more than once.

21 Claims, 7 Drawing Figures

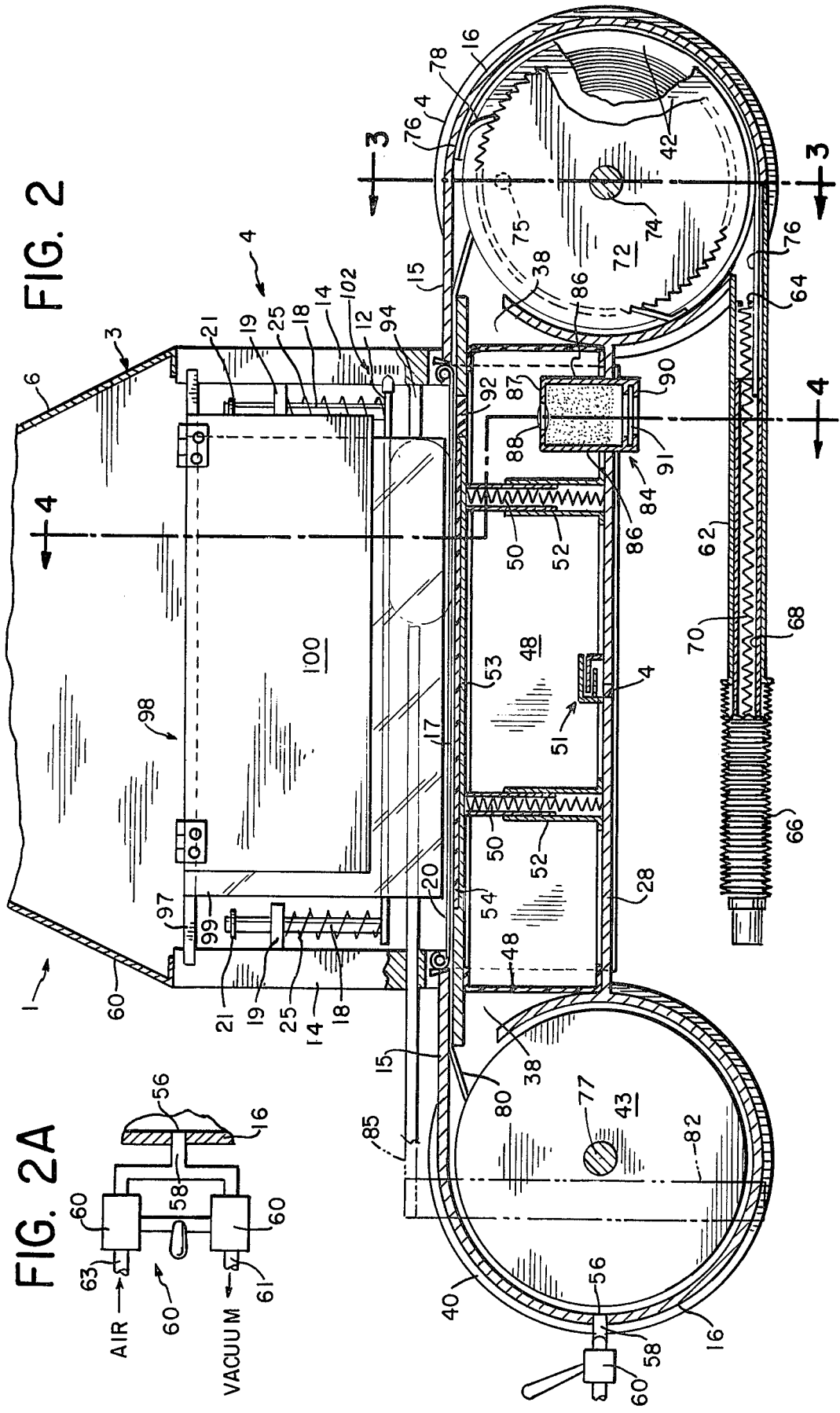
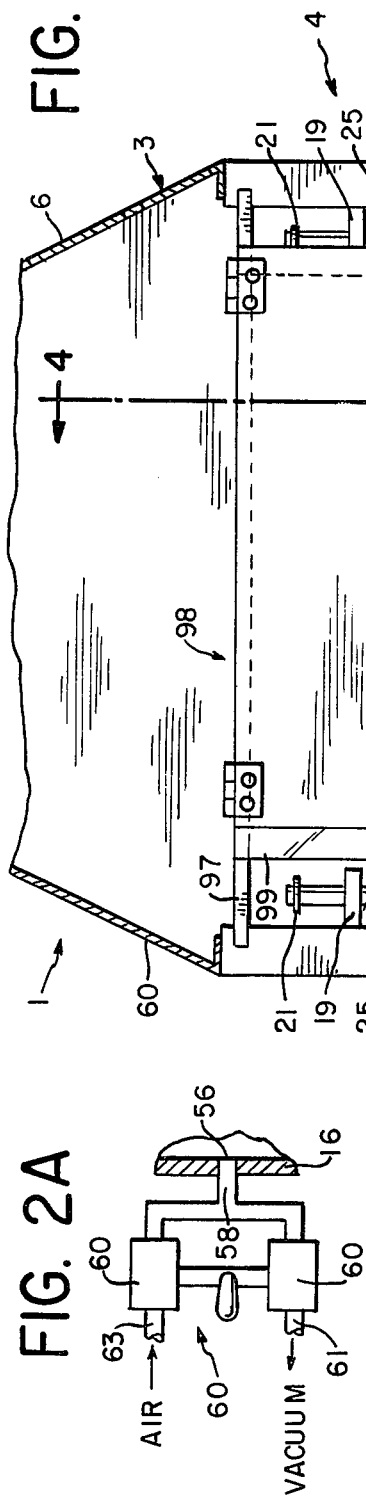

AUTOMATED MAMMOGRAPHY APPARATUS FOR MASS SCREENING

BACKGROUND OF THE INVENTION

Early detection of breast cancer in women is universally recognized as the most effective deterrent to deaths caused by that disease. Women are therefore encouraged to undergo regular medical examinations including breast X-ray on a routine periodic basis. Because of the large female population requiring such X-ray examinations it is desirable to provide a means for X-raying the breasts of large populatons of women as rapidly and economically as possible and producing the required X-rays in a manner suitable for similarly economical and rapid evaluation.

Apparatus for breast X-ray imaging is currently known. In such apparatus a phosphor intensifying screen and a sheet of film with an emulsion sensitive to the light emitted by the phosphor is encased in a thin bag or envelope of material transparent to X-rays. The envelope is air-tight and is evacuated to bring the film and screen into very close contact so that the X-ray image of the breast formed on the screen may be recorded with high resolution on the film. The envelope containing the screen and film is placed below the X-ray apparatus and the breasts of the subject are placed thereagainst after which time the breasts are exposed to X-radiation which penetrates the breasts and causes an X-ray image containing information as to the nature of the tissue within the breasts to be formed on the phosphor screen which image is then recorded on the sheet of film.

Sheet film sizes of at least 8 × 10 inches are generally used and sheet film of this size is relatively expensive. Of substantially greater expense are the intensifying screens employed in the X-ray process. A separate intensifying screen is required for each film package, one film package being required for each exposure. Although the screens are reusable they are quite fragile and often damaged in repeated use, necessitating their frequent replacement. In addition to the expense associated with the use of sheet film and individual screens for each exposure, it is additionally time-consuming and costly to package each sheet of film and screen in a separate envelope, evacuate the envelope and seal it under dust-free and light-free conditions. Furthermore, the time expended in replacing the screen-film envelope after each X-ray exposure limits the number of women who can be accommodated in a mammography mass screening program.

It is known in the art to use smaller areas of film than the conventional 8 × 10 inch film. However, in such prior art systems lenses are used to reduce the full-size image of the breast formed on the screen to a smaller image on the film. It is also known in the art to use electronic means to reduce the image formed on the screen, for example on a cathode ray tube, and to record that image on a small area of photographic film. The use of lenses and/or electronic means to conserve film through reduced image size significantly degrades resolution due to aberrations in the lens and loss of information in the electronic processing. Furthermore, and most important, when a lens is used it is only capable of gathering a small fraction of the light photons forming the image which are emitted by the phosphor screen, so that a large fraction of the light photons containing useful information are lost and not utilized in the mammogram.

SUMMARY OF THE INVENTION

The apparatus of the instant invention overcomes the problems of the prior art to make mammography screening practical on a truly large scale basis by combining high speed of operation with simplicity and reliability of equipment. Maintenance requirements are minimized while high diagnostic quality is provided with minimal exposure to potentially harmful X-radiation. Specifically the instant invention employs a continuous roll of film advanced through a chamber past a permanent stationary image-forming screen and employs a vacuum to both advance the film and to force the film into contact with the image forming screen during X-ray exposures. The chamber is returned to atmospheric pressure to cause film-screen separation prior to advancement of the film for a subsequent exposure. Means are provided for advancing the film after each mammogram by a variable amount dependent on the width of the breast of the last mammogram.

The film has a width of 105 mm. which, applicant has found, can accommodate the breasts of 95% of women who are to be screened.

In addition to the saving in film accomplished by using a roll film with each exposed frame being of significantly smaller size than the sheet film used by the prior art, the use of a roll film preserves the sequence of mammograms on a reel or spool for ease in identification of subjects, filing and classification of mammograms, and speed of inspecting mammograms.

The invention further provides for a removable fence and a shield opaque to X-rays which are used for mammography of the remaining 5% of women whose breast size requires that two X-ray exposures be made to form a mammograph of an entire breast. The fence serves as a stop to position the breast so that the full width of the film is used in the first exposure to accommodate as much of the breast as possible. For the next exposure, the fence is moved away from the breast to permit the breast to overhang the distal edge of the film so that the portion of the breast closest to the rib cage which was not previously X-rayed can be imaged. To prevent reradiation of the previously imaged breast portion during the second X-ray exposure, a shield opaque to X-rays is placed between the X-ray source and the breast. The dimension of the shield in a direction parallel to the depth of the image-forming screen and depth of the breast is the same as the width of the film. The transverse downward extending fence on which there is hinged the distal end of the shield is adapted to be slid into engagement with the frontal portion of the breast and stopped there so that the front portion of the breast already X-rayed during the first exposure is shielded from X-rays during the second exposure.

It is therefore an object of the invention to rapidly record X-ray images of the breasts of a large population of women.

Another object of the invention is to record the X-ray images on a single continuous roll of film.

Still another object of the invention is to record a single breast X-ray high resolution image on a small area of film.

A further object of the invention is to record sequential X-ray images with the use of a permanent X-ray image-forming screen.

Still a further object of the invention is to cause the film on which the X-ray image is to be recorded to engage the image-forming screen during exposures and to separate from the screen for advancement prior to the next exposure.

An additional object of the invention is to X-ray large breasts in portions without subjecting any single breast portion to more than one exposure to X-radiation.

Other and further objects of the invention will be apparent from the following drawings and description of a preferred embodiment in which like reference symbols are used to represent like parts in the various views.

DESCRIPTION OF THE DRAWINGS

FIG. 2 is a rear sectional elevation of the apparatus of the invention in one mode of operation;

FIG. 2A is a plan view in partial section of a part of the apparatus of the invention;

DESCRIPTION OF THE PREFERRED EMBODIMENT

Figure 1:
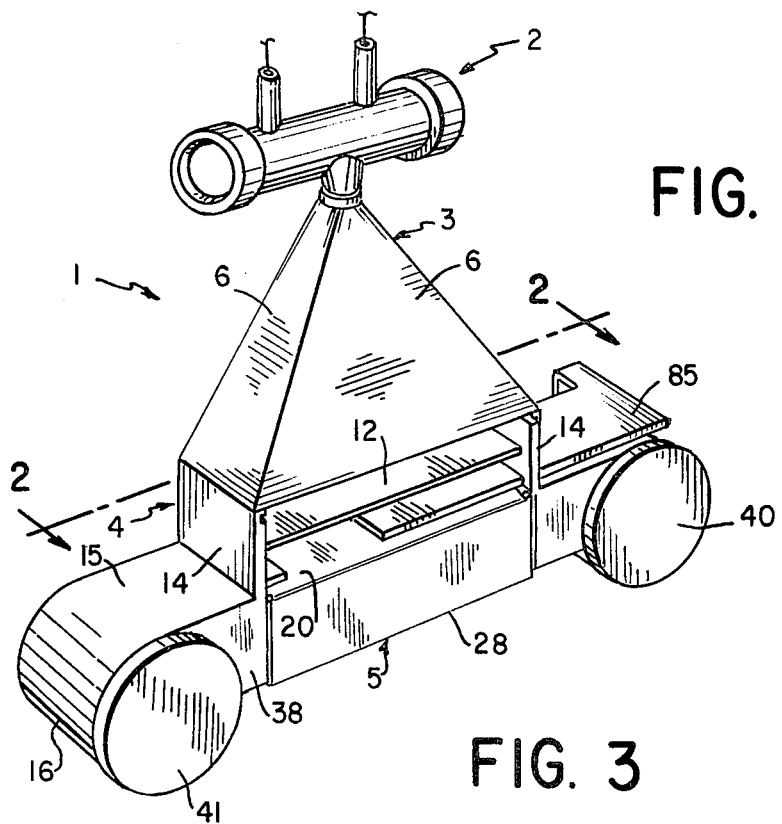
FIG. 1 is a perspective view of the apparatus of the invention.

Referring to FIG. 1 of the drawings, the automated mammography apparatus includes a housing 1 having an upper portion 3 through which X-rays are transmitted from an X-ray source 2 disposed above the housing upper portion 3, a middle portion 4 in which the breasts of the subject being X-rayed are placed during recording of a mammogram and a lower portion 5 which serves, inter alia, as a film cassette for the film on which the mammogram is recorded.

The upper portion 3 of the housing 1 comprises four sidewalls 6 which taper upwardly and inwardly terminating in an apex atop the upper portion 3 upon which the X-ray source 2 is mounted. The sidewalls 6 of the upper housing portion 3 are made of material opaque to X-rays to confine the path of X-rays directed downward from the source 2 toward the middle housing portion 4 within a desired field of view.

The upper housing portion 3 is seated upon sidewalls 14 of the middle housing portion 4. The front of the middle portion 4 as shown in FIG. 1 and the rear of the middle housing 4 are open for access by the subject being X-rayed and the technician taking the X-ray.

The lower housing portion 5 has a shape generally in the form of a film magazine having supply and take-up or storage spools. The middle portion sidewalls 14 are generally transverse to respective upper surfaces 15 of the housing lower portion 5. The exterior of the housing lower portion 5 is generally symmetrical on both sides of the middle portion 4. The upper surfaces 15 of the lower housing portion 5 slope downward into cylindrical portions 16. The cylindrical portions 16 are connected by a flat member 28 forming the floor of the lower housing portion 5 as best seen in FIG. 2.

Figure 4:
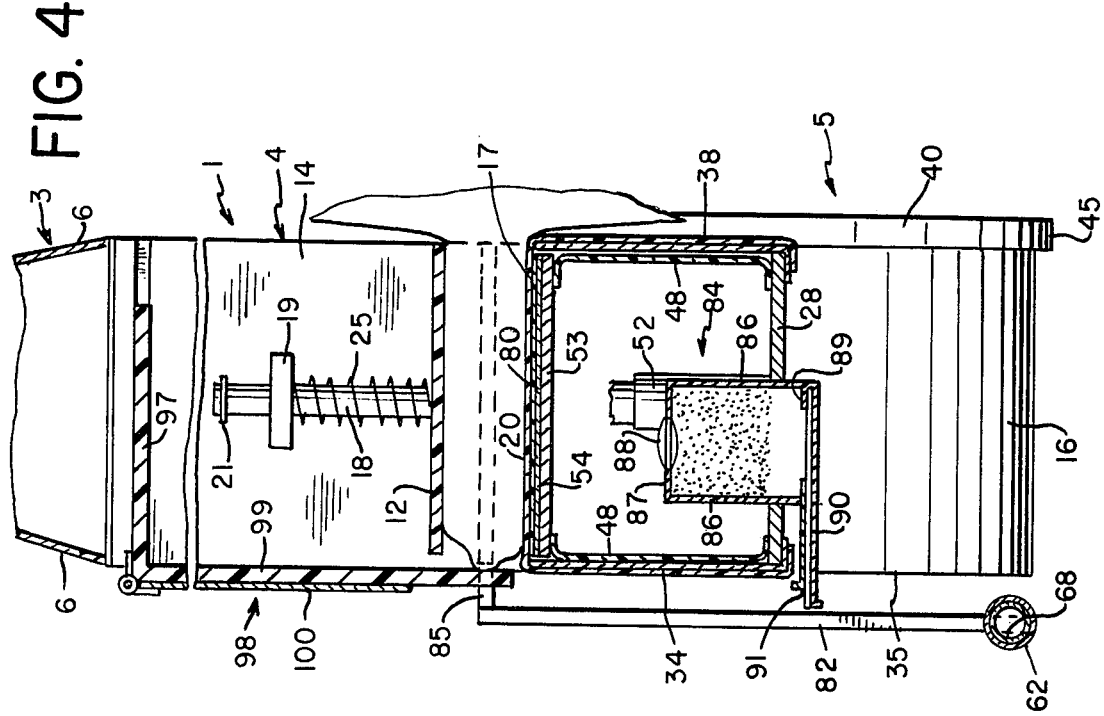
FIG. 4 is a sectional view of the apparatus of the invention taken through line 4—4 of FIG. 2.

Referring now to FIG. 2, substantially coplanar with the surfaces 15 of the lower housing portion 5 and connected thereto with seals 22 to form an airtight fitting therewith is an aluminized mylar sheet 17 which is opaque to visible light but transparent to X-radiation. The length of the mylar sheet measured between the surfaces 15 is substantially equal to the separation of the surfaces 15. The width of the mylar sheet measured from the front of the X-ray apparatus toward its back, that is along the depth of the middle housing portion 4 is slightly greater than the sum of the width of the surfaces 15 measured from front to back and twice the distance from the surface of the mylar sheet 17 to the floor member 28 for reasons which will subsequently be explained. The rear of the lower housing portion 5 is enclosed by coplanar wall members 34 and 35 as best seen in FIG. 4. The front of the lower housing portion 5 includes a front wall 38 similar to the rear wall 34. Removable circular covers 41 and 40 are provided to permit access to a take-up or storage film spool 42 and a film supply spool 43 respectively. The covers 40 and 41 have threaded flange portions 45 which mate with complementary threaded portions on the lower housing portion 5 circumscribing the front edges of the cylindrical wall portions 16.

As can best be seen in FIG. 4 the mylar sheet 17 is folded downward over the front and rear walls 38 and 34 with its lower edges bent inward under floor member 28 of the lower housing portion 5. The previously described dimensions of the mylar sheet permit the mylar sheet to be affixed to the lower housing portion 5 in the manner described. The upper surface of the mylar sheet 17 serves as a window 20 opaque to visible light but (due to its thinness) very transparent to X-rays, and yet strong enough for the breasts of the subject being X-rayed to be supported.

Figure 6:
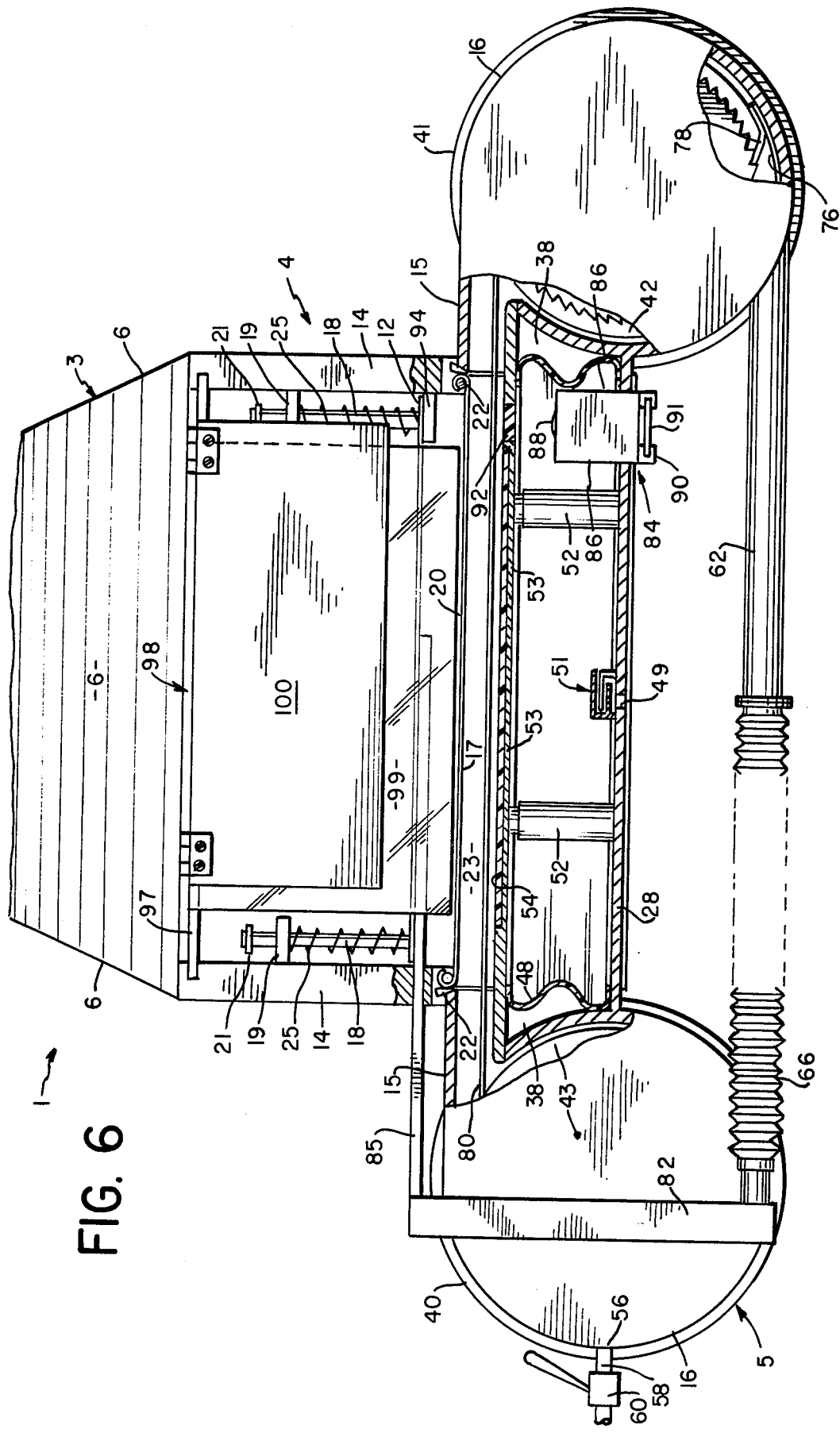
FIG. 6 is a rear elevation of the apparatus of the invention in another mode of operation.

Affixed to the upper surface of the floor 28 of the lower housing portion 5 is a bellows 48 movable upward against the restoring forces of stretched coil springs 50 disposed within hollow tubular columns 52. The coils 50 are attached at their upper ends to the underside of the upper surface of the bellows 48 and at their lower ends to the upper surface of the floor member 28. The springs 50 normally urge the upper surface of the bellows 48 into a downward position as shown in FIG. 6. The floor member 28 of the lower housing portion 5 is provided with a port 49 including a light trap 51 to permit air to escape through the floor member 28 when the bellows 48 is drawn downward as shown in FIG. 6 and to permit air to reenter the bellows when it is desired to move the bellows 48 upward to the position shown in FIG. 2. The light trap 51 prevents exposure of the film to extraneous light as will readily become apparent.

Mounted atop the upper surface of the bellows 48 there is a pressure plate 53 which is slotted to accept a phosphor intensifying screen 54 upon which the mammograph image is formed prior to being recorded on the film. The upper surfaces of the phosphor screen 54 and pressure plate 53 on either side of the phosphor screen 54 are substantially coplanar. The phosphor screen 54 is made from a suitable phosphor which absorbs most of the X-rays and produces a light image suitable for recording on film, as will be known to those familiar with the art. The pressure plate member 53 is substantially rigid to act as a firm support for the phosphor screen 54. As the bellows 48 expands and contracts in a vertical direction the phosphor screen 54 and pressure plate 53 are, together, moved upward toward the mylar window 20 and downward away from the mylar window 20 respectively.

The front wall 38 of the housing 1 is made of a very thin steel sheet of approximately one thirty-second inch in thickness and the edge of the phosphor screen 54 adjacent the front wall 38 is spaced very close to the front wall 38 so that the entire breast, to within less than 1 millimeter of the chest wall, can be placed on the mylar window 20 to be imaged on the mammogram.

The lower portion of the bellows 48 forms an airtight seal with the floor 28 of the lower housing portion 5. An airtight chamber 23 encloses the space between the mylar window 20 and coplanar surfaces of the pressure plate 53 and phosphor screen 54, which space extends about the exterior of the belows 48 within the chamber walls 34 and 38 and into cylindrical chamber portions 16 of the lower housing 5. The chamber 23 is tightly sealed from the external atmosphere. Referring to FIGS. 2 and 2A, an opening 56 is provided in the outward facing portion of the cylindrical wall 16 adjacent the film supply spool 43 to receive a pipe 58 leading to a two-way valve 60. The two-way valve 60 has one input 61 to which a standard vacuum pump (not shown) may be connected and another input 63 which may be exposed to the ambient atmosphere. The valve 60 may be switched to one position in which the vacuum pump is connected to the pipe 58 for evacuating the air within the airtight chamber 23 and to another position for admitting ambient air to the airtight chamber 23.

The atmospheric input of the valve 60 is provided with a filter to prevent dust (which often causes artifacts on mammograms) from entering the vacuum film chamber 23. Should any dust inadvertently enter the chamber, it is pumped out of the chamber when the chamber 23 is again evacuated preparatory to the next exposure.

The screen 54 instead of being placed on the pressure plate 53 can be placed on the underside of the mylar window 20. The pressure plate 53 would then press the film 80 against the underside of the screen as the chamber 23 was evacuated. However, while such apparatus is entirely workable and is within the scope of the instant invention, it has been found that the relatively fragile screen is less subject to damage when placed on the pressure plate 53. Moreover, it has also been found that the amount of X-ray exposure required to form an image is less when the screen is below the film than when it is above the film.

The inward facing portion of the cylindrical wall 16 adjacent the take-up or storage spool 42 is apertured to receive a rigid airtight cylindrical sleeve 62, having interior transverse shoulder portions 64. Affixed to a flange at the end of the cylindrical sleeve 62 distant from the take-up spool 42 and forming an airtight seal therewith is a bellows 66 compressible and expandable along an axis parallel to that of the cylindrical sleeve 62. The left end of the bellows 66 as shown in FIG. 2 is sealed about the circumference of an inner cylindrical sleeve 68 slidable within the outer cylindrical sleeve 62. A normally compressed coiled spring 70 has one end abutting the shoulder portions 64 and an opposite end abutting an interior surface of the inner sleeve 68. The compressed spring 70 normally urges the inner cylindrical sleeve 68 toward the left as seen in the view of FIG. 2, that is toward an expanded position. Evacuation of the space within the bellows 66 causes the bellows 66 to contract. As the bellows 66 contracts it forces the inner sleeve 68 to slide to the right in the view of FIG. 2 against the opposing force of the spring 70. The spring constant of the spring 70 is chosen so that the evacuated bellows will overcome the spring force while the spring force will be sufficient to restore the bellows to its expanded position when the space within the sleeves 68 and 62 is at atmospheric pressure.

Figure 3:
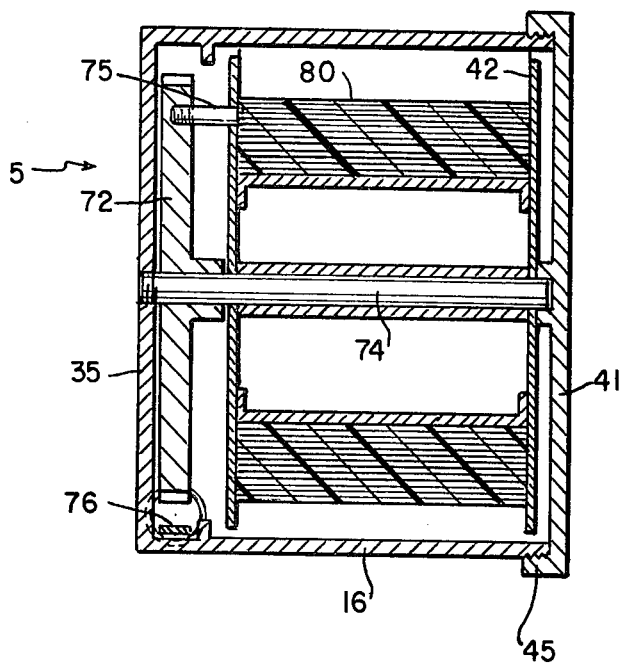
FIG. 3 is a sectional view of the apparatus of the invention taken through line 3—3 of FIG. 2.

Referring now to FIGS. 2 and 3 a gear 72 and take-up spool 42 are drivingly connected for rotation together about a shaft 74. The take-up spool 42 is connected to the gear 72 by a stud 75. The gear 72 and take-up spool 42 are mounted on the common shaft 74 for rotation thereon.

A resilient band 76 of spring steel or the like has one end fixedly connected to the inner sleeve 68 as shown in FIG. 2 and extends into the cylindrical portion of the lower housing 5 adjacent the take-up spool 42, bending about the circumference of the gear 72 and terminating in a hook-like portion 78. The hook-like portion 78 of the resilient band 76 serves as a pawl member for gripping the teeth of the gear 72. The teeth of the gear 72 and the pawl member 78 are mutually disposed so that the pawl member 78 can slip over the teeth of the gear as the pawl member 78 moves in a counter clockwise direction as shown in the view of FIG. 2 while clockwise movement of the pawl member causes the gear 72 to rotate clockwise with the pawl member 78.

The lower housing portion 5 is loaded with a roll of film as follows: the air valve 60 is switched so that the airtight chamber 23 within the lower housing portion 5 is in communication with the ambient atmosphere. As a result of the ambient pressure within the chamber 23 the pressure plate 53 and screen 54 are maintained in a downward position and the bellows 66 is expanded to the left as shown in the view of FIG. 6. The lower housing circular covers 40 and 41 are removed to provide access to the interiors of the cylindrical portions of the lower housing portion 5, within which there are a supply spool spindle 77 and the take-up spool spindle 74 respectively. A spool 43 having wound thereon a roll of unexposed film 80 is placed onto the supply spindle 77. The film 80 is provided with a paper leader which is pushed through the space between the mylar window 20 and phosphor screen 54 into the space adjacent the take-up spool 42. The forward end of the paper leader is threaded into a slot in the take-up spool 42 and the spool 42 is rotated by hand to fix the leader in place in the slot. The covers 40 and 41 are then threaded onto the lower housing portion 5 leaving the film in complete darkness within the chamber 23.

The film 80 desirably used is supplied by its manufacturer with an interleaved roll of thin black paper which serves as a backing to protect the emulsion of the film from scratches which produce artifacts, a common occurrence when layers of film are wound one on top of the other. A long paper leader is also supplied at the beginning of the film roll and a similar paper trailer at the end of the film roll to prevent exposure to light during loading and unloading. The major portion of the leader is slightly wider than the film width and presses tightly against the flanges of the supply spool 43 to form a light-tight covering for the film. This permits the film to be loaded into the lower housing portion 5 in a lighted room. The trailer also protects the film from light so that the take-up reel 42, upon which there is wound a complete roll of exposed film, may be removed in a lighted room.

To further enhance the light shielding effect of the paper leader and trailer, the inner surfaces of the flanges of the spool 42 and 43 are covered with black felt. The removable covers 40 and 41 are light-tight and airtight so that when the chamber 23 is evacuated the vacuum is easily maintained. The interior of the chamber 23 in addition to being airtight is also completely shielded from outside light.

The initial 300 mm. of the paper leader, in front of the widened paper leader portion, is narrower than the film width and relatively stiff so that during loading of the film the leader is readily inserted through the space between the mylar window 20 and screeen 54 and into the slot on the take-up spool 42.

To advance the film 80 from the supply spool 43 to the take-up spool 42 the valve 60 is switched to vacuum at which time the air in the airtight chamber 23 is evacuated. That is, the air is pumped from within the bellows 66, the sleeves 62 and 68, the area about the take-up spool 42, the space between the mylar window 20 and screen 54, and the space adjacent to the film supply spool 43, and out through the pressure line 58. This evacuation causes the bellows 66 to contract. Contraction of the bellows 66 toward a position as shown in FIG. 2 forces the inner sleeve 68 to move rightward with respect to the outer sleeve 62 in the view of FIGS. 6 and 2 thereby pushing the spring steel band 76 about the gear 72 with the pawl member 78 slipping in a counter clockwise direction over the teeth of the gear 72. When maximum contracton of the bellows 66 is reached the pawl member 78 occupies an uppermost position as shown in FIG. 2.

Evacuation of the space between the mylar window 20 and screen 54 creates a pressure differential between the space in the bellows 48 below the pressure plate 54, which is exposed to atmospheric pressure through the port 49, and the space above the pressure plate 54 which is under vacuum. The net pressure differential between the two last mentioned spaces results in a net force urging the pressure plate 53 with screen 54 upon it upward against the downward force of stretched coil springs 50. As a result of the foregoing the film paper leader extending from the supply spool 43 to the take-up spool 42 is sandwiched between the underside of the mylar window 20 and upper surface of the screen 54 and there held in a flat plane suitable for recording the image formed on the phosphor screen 54. It will be recognized that no X-ray image may be recorded while the paper leader is above the screen 54 and that the image can be recorded only when the film 80 has been advanced sufficiently so that the paper leader is beyond the field of view of the screen 54.

The air valve 60 is again switched so that atmospheric pressure is applied to its inlet and thereby to the space 23 and the space within the interior of the bellows 66. Under atmosphere, the bellows 66 is pushed leftward to the position shown in FIG. 6 by the spring 70 and the inner sleeve 68 is pushed leftward with respect to the outer sleeve 62. As the inner sleeve 68 moves leftward it pulls with it the spring steel band 76 causing the gear wheel 72 to rotate clockwise in the views of FIGS. 2 and 6, thereby advancing the paper leader (and eventually the roll of film which follows) between the mylar window 20 and screen 54 onto the take-up spool 42. As can be seen from FIGS. 2 and 6 the degree of clockwise movement of the gear 72 and hence of the take-up spool 42, which degree of movement determines the amount of film wound onto the take-up spool 42, is a function of the magnitude of leftward displacement of the inner sleeve 68 relative to the outer sleeve 62 during expansion of the bellows 66. The maximum expansion of the bellows 66 is limited by a vertical stop member 82 fixedly connected to a horizontal plate 85 slidable within one or more slots in the left sidewall 14 of the middle housing portion 4. The assembly which comprises the vertical stop member 82 and horizontal plate 85 will be described subsequently.

When the airtight chamber 23 is connected to atmosphere the springs 50 urge the pressure plate 53 with phosphor screen 54 thereon downward so that air flows into the space between the screen 54 and mylar window 20 and the pressure plate 53 moves downward to the positon shown in FIG. 6 wherein the pressure plate 53 rests upon the edges of cylindrical wall portions 16. To insure that the pressure plate 53 can be moved downward when the airtight chamber 23 is connected to atmosphere, additional air connections from the valve 60 may be made through the lower housing portion surfaces 15 or the mylar window 20 to further enable incoming air to fill the space between the screen 54 and film 80. It has been found, however, as a practical matter, that even with the screen 54 in intimate contact with the film 80 against the mylar window 20 there is sufficient separation at points between the screen 54 and film 80 to permit incoming air to fill the space between the screen 54 and film 80 thereby allowing the springs 50 to pull the pressure plate 53 down.

As the pressure plate 53 is lowered the air within the bellows 48 which would otherwise resist downward motion of the pressure plate 53 is permitted to escape through the port 49. The light trap 51 prevents the film 80 from being exposed to light entering the port 49.

With the pressure plate 53 in the downward position shown in FIG. 6 the film 80 is free to advance from the supply spool 43 to the take-up spool 42 without scraping against any surface which may cause artifacts to be observed on the developed mammogram. The valve 60 is alternately switched between vacuum and atmospheric pressure to advance the film to the point where the paper leader is wound onto the take-up spool 42 and the emulsion surface of the film is disposed beneath the mylar window 20. As previously noted the mylar window 20 is opaque to visible light but transparent to X-rays so that no image is recorded on the film 80 until the X-ray source 2 is energized.

Mounted within the floor member 28 of the lower housing portion 5 is a patient identification recording assembly 84. The identification assembly 84 comprises a box-like structure best seen in FIGS. 2 and 4. The patient identification assembly 84 has four sidewalls 86, a top 87 which is apertured to receive a lens 88, an apertured floor member 89 connected to the bottoms of the walls 86, a slide 91 which is suitably shaped so it is light-tight both when slid in and when slid out, and a lower supporting surface 90 parallel to and spaced beneath the floor member 89. The floor member 89 and support 90 extend in parallel spaced relationship rearward of the lower housing portion 5 with the space between the member 89 and card support 90 defining a slot in which the slide slides in or out. The patient identification card has typed on its surface information unique to the subject whose mammograph is being recorded. It is placed on the slide while the slide is slid out, and then the slide with card thereon is slid in. The patient identification unit 84 and the axis of the lens 88 are mutually disposed so that light falling on a patient identification card inserted on the slide of the unit 84 will be reflected from the upper surface of the identification card through the lens 88 and focussed on the film through a plexiglass window 92 in the pressure plate.

The sidewalls 86 of the identification assembly 84 are partially transparent to X-rays and have their inner surfaces coated with a phosphor or any other substance which is fluorescent when bombarded with X-rays. When the X-ray source 2 is energized some X-rays are transmitted through the upper housing portion 3 downward through the mylar window 20, screen 54 and pressure plate 53, and through the walls 86 and top 87 of the identification unit 84, thus causing the interior of the identification unit 84 to become illuminated as a result of the X-rays impinging on the fluorescent material on the walls 86. The resultant light within the identification unit 84 is incident upon the upper surface of the patient identification card which is inserted on the slide therein and disposed directly beneath the aperture in the floor 89. The incident light is reflected from the upper surface of the identification card upwardly through the lens 88 which focusses a reflected light image of the identification card on the film. It is to be noted that the image of the identification card is formed on the film only when the X-ray source 2 is energized, that is, only when the X-ray exposure for the mammogram is made. The identification card may be made of paper or cardboard on which the patient information is typed.

The middle housing portion 4 of the X-ray apparatus in which the breasts of the subjects to be X-rayed are placed during recording of the mammogram will now be described. Extending inward from the sidewalls 14 are shoulder members 19 which are apertured to receive guidepins 18 slidable therethrough. The guidepins 18 are provided at their upper ends with circular flange portions 21 to limit downward movement of the guidepins 18. The lower ends of the guidepins 18 are affixed to a breast compression plate 12. The breast compression plate 12 may be made of a substantially rigid material substantially transparent to X-rays such as a suitable thin plastic. The compression plate 12 is movable upwardly and downwardly with the guidepins 18. The clearance between the guidepins 18 and the apertures in the shoulder member 19 is kept small to minimize skewing of the guidepins 18 with respect to the shoulder members 19 so that the pressure plate 12 maintains its orientation parallel to the mylar window 20 during upward and downward movement. Coil springs 25 are disposed about the guidepins 18 and are compressed between the shoulder portions 19 and the upper surface of the breast compression plate 12. The compressed coil springs 25 urge the compression plate downward toward the mylar window 20.

Extending from the right vertical wall 14 as seen in the view of FIG. 2 is a stationary shield 94 which is opaque to X-radiation. The shield 94 is disposed above the patient identification assembly 84 and prevents X-rays from the X-ray source 2 from impinging directly upon the film immediately above the identification assembly. Thus the film area beneath the shield 94 is exposed only from light directed upward through the lens 88 from the patient identification assembly 84. The shield 94 is located a distance above the mylar window 20 substantially equal to the distance from the center of a breast of average size, placed on the mylar window and compressed under the downward force of the compression plate 12, to the mylar window 20. The inward edge of the shield 94 serves as a lateral stop for locating the breast to be X-rayed on the mylar window 20.

The horizontal plate 85 serves as a movable shield and is made of brass or any other material opaque to X-rays. The slot in the left vertical wall (as seen in the view of FIG. 2) in which the movable shield 85 is slidable toward and away from the stationary shield 94 is located at a height from the mylar window 20 substantially equal to the height of the stationary shield 94 from the mylar window 20.

In use, the breast of the subject is placed upon the mylar window 20 with one side of the breast abutting the inward edge of the shield 94. The slidable shield 85 is then slid toward the breast until its inward edge just touches the opposite side of the breast. This positioning of the movable shield 85 results in the vertical stop member 82 occupying a position to limit expansion of the bellows 66 so that the amount of film advanced following the recording of the next mammogram is only slightly greater than the sum of the width of the breast, that is the distance between the inward edges of the shields 85 and 94, and the width of the film area beneath the shield 94 upon which the identification card data is recorded.

Figure 5:
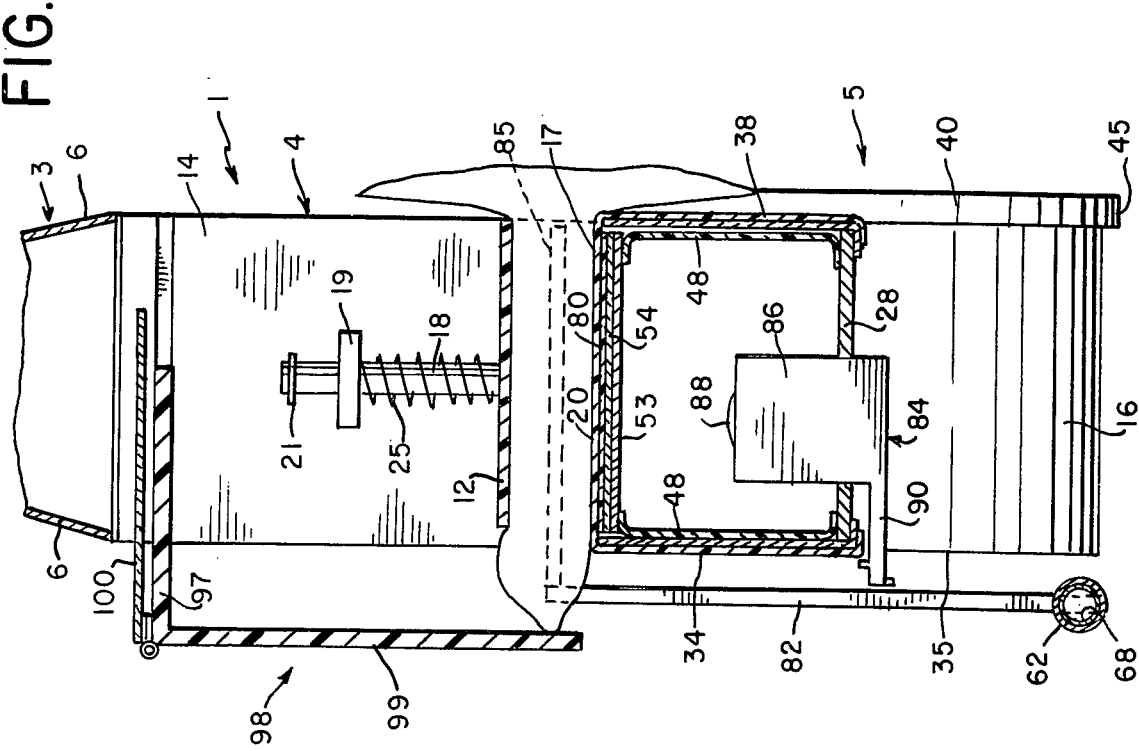
FIG. 5 is a side elevation of the apparatus of the invention in partial section as used for a second X-ray of an oversize breast.

Referring now to FIG. 5, the upper portions of the sidewalls 14 of the middle housing portion 4 are slotted in a direction transverse to the slot for the shield 85 to receive the horizontal portion 97 of a fence assembly 98 which has a vertically downwardly extending fence portion 99. The portion 97 is made of a material opaque to X-rays and contains a large aperture whose dimensions allow an X-ray beam of correct size to illuminate the entire screen 54 to pass through. The fence assembly 98 is slidable from the rear of the middle housing portion 4 inwardly toward the front thereof. The vertical fence portion 99 extends downward a distance sufficient so that as the fence assembly 98 is slid inward toward the front of the X-ray apparatus by the maximum degree possible as shown in FIG. 4 the vertical fence portion 99 prevents a breast, inserted into the middle housing portion 4 from the front side of the X-ray apparatus and positioned on the mylar window 20, from overhanging the useable film area. That is, as the breast is moved inward from the front of the X-ray apparatus toward the rear it will not be permitted to extend beyond the film edge most distant from the chest of the subject being X-rayed. This limiting position of the fence assembly 98 is best seen in FIG. 4.

Hinged at the outer intersection of the horizontal member 97 and vertical member 99 of the fence assembly 98 is a shield 100 made of a material opaque to X-rays such as brass. The shield 100 normally occupies a downward position as shown in FIG. 4 in which position it is out of the X-ray field of view. The height of the shield 100 as shown in FIG. 4 measured from the hinge to the bottom edge of the shield is substantially equal to the usable width of the X-ray film. Hence when the shield 100 is rotated to a horizontal position atop the horizontal member 97 as shown in FIG. 5 and the nipple of the breast is pressed against the vertical fence member 99 the shield 100 prevents X-rays from reaching a portion of the breast having a depth, measured from the nipple toward the rib cage, equal to the usable film width. As shown in FIG. 5, the fence assembly 98 is slid rearward just permitting the breast to be fully inserted in the middle housing portion 4 so that only the portion of the breast closest the subject's chest and beyond the film width measured from the nipple is exposed to X-rays. The fence and shield are used in the position shown in FIG. 5 to make a second X-ray exposure of a breast too large to be X-rayed in a single exposure as will hereinafter be described.

The sequence of operation of the apparatus of the invention is generally as follows. Initially the covers 40 and 41 are removed and a fresh spool 43 upon which unexposed film is wound is mounted on the spindle 75. The paper film leader is threaded between the mylar window 20 and screen 54 which are spaced apart due to the pulling force of the springs 50. The film leader is then threaded onto the take-up spool 42 through a slot provided therein as previously described. The covers 40 and 41 are then replaced and the valve 60 is switched back and forth between atmosphere and vacuum to advance the paper leader through the space 23 a predetermined number of times according to the length of the paper leader until the beginning of the emulsion of the film 80 is positioned within the X-ray field of view, that is within the space between the screen 54 and mylar window 20.

The identification card of the first patient is inserted in the slot in the patient identification assembly 84, after which the valve 60 is switched to vacuum. As the space 23 is evacuated the bellows 48 is drawn upward against the force of the springs 50 forcing the screen 54 to press the film 80 against the mylar window 20. Simultaneously the bellows 66 contracts against the force of the spring 70, moving the ratchet pawl 78 counter-clockwise in preparation for the winding of the film subsequent to the X-ray exposure.

The patient is then seated in front of the X-ray apparatus and her breast is positioned on the mylar window 20. At this time the fence assembly 98 is slid fully into the upper slots in the housing walls 14 to a position as shown in FIG. 4 with the shield 100 pivoted downward. The patient inserts her breast fully into the middle housing portion 4 toward the vertical fence member 99 while the compression plate 12 is held upward against the force of the springs 25 to permit the breast to be positioned on the mylar window 20.

The subject is instructed to move forward until her chest reaches the front wall 38 of the housing 1 or until the nipple of the breast touches the inner surface of the vertical fence member 99. If the nipple of the breast touches the vertical fence member 99 before the patient's chest is immediately adjacent the frontal wall 38 the patient can be instructed to press the breast against the vertical fence portion 99, if possible, until the chest is adjacent the front wall 38. If the breast is too large to be placed within the space between the inner surface of the vertical fence member 99 and the front wall 38 a second exposure will be required for the portion of the breast nearest the subject's chest, which breast portion is unable to fit beyond the front wall 38.

With the breast placed as far into the middle housing portion 4 as possible but not extending beyond the vertical fence 99 the compression plate 12 is gently lowered to flatten the breast on the mylar window 20 to enhance the mammogram. It is to be noted that the breast is positioned with its left side adjacent the inward edge of the shield 94. After the compression plate 12 is lowered compressing the breast the movable shield 85 is slid toward the breast until its edge abuts the right edge of the breast. The dimensions of the gear wheel 72, the sleeve 62 and the bellows 66 are such that the amount of the film that will be wound onto the takeup spool 42, when the bellows expands from its maximum contracted position as shown in FIG. 2 to the point where it engages the surface of the vertical stop 82 as shown in FIG. 6, is slightly greater than the sum of the width of the compressed breast measured between the inner edges of the shields 85 and 94 and the length, measured in the direction of film advancement, of the film area beneath the shield 94 upon which the patient identification data is recorded.

In order to insure that the length of film advanced for a given angular rotation of the take-up spool 42 remains substantially constant with build-up of film on the take-up spool 42, a large diameter take-up spoool 42 is used. By using a take-up spool 42 having a diameter of approximately 150 millimeters with 300 feet of film wound thereon, although the film thickness builds up on the take-up spool 42 with each winding of the film, the amount of increase in spool-plus-film diameter from beginning to end of the film relative to the spool diameter is insubstantial due to the large diameter of the spool and the thinness of the film wound on it. By maintaining the effective spool-film diameter substantially constant, a simplified film advance mechanism is possible wherein the gear 72 rotates through a constant angle for a given amount of film advance. This eliminates the need for the more complex mechanism of a metering roller to vary angular rotation for controlling film advance. A further advantage of the use of a large diameter take-up spool is that the amount of bending stress to which the emulsion on the film is subjected is minimized thereby preventing damage to or fracture of the emulsion.

With the movable shield 85 properly in place against the right edge of the breast, the X-ray source 2 is energized causing X-rays to be directed through the breast and forming an X-ray image on the phosphor screen 54 immediately beneath the breast. Simultaneously, an image of the information typed on the upper surface of the identification card is formed on the film 80 adjacent to the breast image and beneath the shield 94. After the X-ray exposure is completed, the pressure plate 12 is raised. If the breast was small enough to be entirely X-rayed with a single exposure, the subject may be positioned for an exposure of the other breast or the same breast may be exposed from a different angle.

Preferably, both a cranio-caudal view and a lateral view are taken of each breast. The lateral view can be taken by leaving the apparatus in the same vertical orientation as shown in the drawings by merely having the patient bend her torso sideways. This has been found to be the most efficient way of obtaining mammograms of both the cranio-caudal and lateral views. The apparatus, however, can be provided with conventional means for rotating it into a horizontal plane about a pivot point near the center of the mylar window 20. With this alternative the cranio-caudal view would first be taken with the apparatus in an upright position as shown in the drawings and the apparatus would then be rotated 90 degrees for the lateral view.

If the exposure last taken was for the last mammogram view of the patient, the patient may be excused and the next patient brought in to the X-ray room. However, if the breast was too large to fit within the field of view in the middle housing portion 4, that is the space between the vertical fence 99 in the position shown in FIG. 4 and the front wall 38, a second exposure is made of the portion of the breast not previously X-rayed as follows.

The fence assembly 98 is slid rearwardly and the shield 100 is pivoted to a horizontal position as shown in FIG. 5. With the fence assembly 98 withdrawn rearward of the middle housing portion 4 the subject is instructed to approach the front wall 38 until her chest is immediately adjacent the front wall 38 so that the portion of the breast previously unexposed to the X-rays now lies within the X-ray field of view. At this time the nipple and adjacent porion of the breast will overhang the rear end of the mylar window as shown in FIG. 5. The fence assembly 98 is then slid frontward toward the breast until the vertical member 99 abuts the nipple of the breast as shown in FIG. 5. Since the length of the shield 100 is equal to the width of the film, the front portion of the breast, measured from the nipple toward the chest a distance equal to the width of the film, will be shielded from the X-rays during the second exposure.

It is to be observed that this front portion of the breast is the portion of the breast X-rayed during the first exposure. During the first exposure the portion of the breast adjacent the subject's chest which cannot be fitted within the X-ray field of view is not exposed to X-rays. Hence during the two exposures necessary for mammography of a very large breast, no single portion of the breast is exposed to X-rays more than once.

Following each X-ray exposure the valve 60 is switched to atmospheric pressure to lower the pressure plate 53 and then advance the film 80 for the next exposure, and then switched back to vacuum to reposition the pressure plate 53 against the film 80 while contracting the bellows 66 so that the movable shield 85 may be positioned according to the width of the next breast to be X-rayed.

As has been previously indicated, the 105 mm. film width which is substantially less than that of the sheet film used in the prior art, is sufficient to accommodate most women and therefore results in substantial film cost savings. The savings is compounded by the provision for variable film advance according to breast width as previously described.

Studies made at The Charles and Stella Guttman Breast Diagnostic Institute have revealed that the breasts of 80% of women have a rib to nipple dimension of less than 105 mm. and are therefore easily accommodated by an X-ray field of view of 105 mm. by 250 mm. It has further been found that another 15 percent of the breasts of women, although exceeding the 105 mm. film width, can easily be made to fit within the field of view of the apparatus merely by bending the breast slightly sideways and thereby decreasing the effective breast dimenson in the direction parallel to the width of the film, that is, perpendicular to the chest of the subject. This increases the dimension of the breast parallel to the length of the film 80 but in virtually all such cases the 250 mm. length dimension of the field of view is sufficient. The above mentioned studies at The Charles and Stella Guttman Institute thus indicate that 95% of all women may have their breasts mammographed with a single X-ray exposure on 105 mm. X-ray film.

In the remaining 5% of cases where the breast size is too great to fit within the 105 mm. × 250 mm. field of view, each mammogram is recorded with two exposures as previously described. Upon the completion of the second X-ray exposure the fence assembly 98 is returned to its original positon as shown in FIG. 4.

The degree of X-ray exposure necessary to obtain an acceptable mammogram varies with breast thickness. The greater the breast thickness the greater the amount of X-ray exposure required. In order to facilely determine the breast thickness and proper exposure to X-rays, a scale 102 can be mounted on the right sidewall 14 as shown in FIG. 2. The scale may have units of length such as inches to measure breast thickness and may also have units of time during which the X-ray source is to be energized for the given breast thickness. An indicator pointer or line on the compression plate 12 may be provided to read breast thickness and exposure time. The upper or lower edge of the compression plate 12 may serve as the indicator line. Thus once the compression plate is released to compress the breast, the technician may obtain a direct reading of the thickness of the compressed breast and the proper time to which the breast is to be exposed to X-rays in order to obtain a properly exposed mammogram.

The 105 mm. film used in the preferred embodiment has a length of approximately 300 feet and is able to accommodate approximately 125 women without reloading. After the last exposure is made on the film 80, the valve 60 is switched between atmosphere and vacuum several times to advance the film through the chamber 23 followed by the paper trailer until the film and trailer are completely wound onto the take-up spool 42. The cover 41 is then removed and the film is unloaded. A new unexposed roll of film is then loaded into the lower housing portion 5 as previously described and mammograms of the next group of women may then be recorded.

The entire length of the exposed film is developed without severing the individual mammograms and once developed can be passed through an illuminated viewer of conventional design to rapidly read the mammograms in sequence. The identification data associated with each patient appears next to each mammogram so that the reader can instantly discern the condition of a specific subject.

It is to be recognized that variations from the details of the preferred embodiment herebefore described may be made without departing from the spirit and scope of the invention which is to be limited only by the claims which follow. For example, while film widths of 105 millimeters have been found convenient and commercially available, films of other widths may be used. The orientation of the apparatus may be changed and the direction of movement of the film advanced mechanism may also be altered while achieving the desired function.

What is claimed is:

1. Apparatus for recording an image of the breast of a woman on a film comprising:

a surface member having a surface adapted to support the breast while exposed to energy for irradiating the breast to form an image of the breast in a plane spaced from said supporting surface;

means for urging said film into the plane of said image for recording said image on said film;

means for supplying a continuous roll of said film for recording images therealong;

take-up means for sequentially storing sections of said film after each section has an image recorded thereon;

movable transport means for advancing said film from said supply means to said take-up means; and means for selectively evacuating the space between said film and said film urging means for moving said film urging means into a first position in contact with said film and for repressurizing said space to move said film urging means to a second position displaced from said film;

said transport means being responsive to the pressure between said film and said urging means so that said film is advanced only when said urging means is in a position other than said first position.

2. Apparatus for recording an X-ray image of the breast of a woman on film comprising:
   a source of X-rays for irradiating the breast,
   a substantially flat surface member, in spaced relation to said X-ray source, against which the breast is supported for recording said X-ray image;
   a screen having a surface upon which the X-ray image is formed, said image forming surface being adjacent and parallel to said flat supporting surface at least during the recording of said X-ray image, said X-rays impinging on said screen after passing through the breast to form said X-ray image;
   a substantially airtight chamber adapted to have a pressure applied thereto and maintained therein;
   means for urging said film into intimate contact with said screen for recording said image on said film;
   means for supplying a continuous roll of said film for recording X-ray images therealong;
   take-up means adapted to be rotated for sequentially storing sections of said film after each section has an X-ray image recorded thereon;
   transport means for rotating said take-up means; and
   means for moving said film urging means between a first position in intimate contact with said film and pressing said film against said image-forming screen and a second position displaced from said film;
   said transport means and moving means for said film urging means being responsive to the pressure in said chamber so that said film is advanced only when said urging means is in a position other than said first position.

3. Apparatus according to claim 2 wherein said screen is mounted on said urging means.

4. Apparatus according to claim 2 wherein said breast support means comprises said screen.

5. Apparatus according to claim 3 wherein said chamber has an upper outer surface comprising said supporting surface and a lower movable surface comprising said urging means, and further including means for selectively reducing and increasing the pressure in said chamber, said urging means being movable to said first position in response to a reduction in pressure in said chamber and to said second position in response to an increase in pressure in said chamber.

6. Apparatus according to claim 5 wherein said supply means and said take-up means are disposed in said airtight chamber.

7. Apparatus according to claim 5 wherein said urging means is mounted on a bellows forming a portion of said chamber and displaceable in a direction to move said urging means toward said first position as said chamber pressure is decreased in response to the pressure differential between the interior and exterior of said bellows, and to move said urging means toward said second position when the pressure in said chamber is increased.

8. Apparatus according to claim 2 further comprising masking means movably mounted relative to the breast for masking the film area within the field of view of said X-ray source extending beyond the width of the breast being imaged, said masking means limiting movement of said transport means so that the length of film travel during film advancement is a function of the size of said imaged breast.

9. Apparatus according to claim 2 further comprising means for compressing the breast against said flat surface.

10. Apparatus according to claim 9 further comprising means for measuring the thickness of the breast, including a scale and a pointer movable relative to said scale, one of said scale and said pointer being fixedly mounted relative to said breast compressing means for movment therewith, and the other of said scale and said pointer being fixedly mounted relative to said breast supporting surface.

11. Apparatus according to claim 10 wherein said scale indicates the degree of desired X-ray exposure for a breast of the measured thickness.

12. Apparatus according to claim 3 further comprising positioning means having a surface substantially transverse to said supporting surface adjacent the edge of the film most distant from the chest of the woman whose breast X-ray is being recorded to prevent the breast from extending beyond the area of said film upon which said X-ray image is to be recorded.

13. Apparatus according to claim 12 wherein said positioning means is movable to permit the breast to extend beyond said film recording area.

14. Apparatus according to claim 3 further comprising means for shielding a portion of the breast from exposure to said X-ray source, said shielding means having a surface substantially opaque to X-radiation and movable between a position within the path of at least some of the X-rays emitted from said source toward the breast and a position removed from said path and having another surface transverse to said shielding surface adapted to engage the breast when the shielding surface is in a position to shield said portion of the breast.

15. Apparatus according to claim 14 wherein the dimension of said shielding surface parallel to the width of said film when said shielding surface is in said X-ray path is substantially equal to said film width.

16. Apparatus for recording an X-ray image of the breast of a woman on film comprising:
   a flat surface member for supporting the breast;
   a source of X-rays mounted above said surface member and adapted to cause said X-rays to be incident thereon;
   a housing disposed beneath said flat supporting surface member, said housing including a substantially airtight chamber;
   means for changing the pressure in said airtight chamber from a first pressure level to a second pressure level;
   a first pressure responsive surface member in said airtight chamber occupying a first position corresponding to said first pressure level and movable to a second position corresponding to said second pressure level, at least one of said support surface member and said pressure responsive surface member including a surface adapted for having formed thereon said image,
   film supply means disposed in said airtight chamber,
   film take-up means disposed in said airtight chamber, said film extending from said film supply means to said film take-up means,
   means for advancing said film from said supply means to said take-up means, including second pressure responsive movable member occupying a first position corresponding to said pressure level and a second position corresponding to said second pressure level and means operatively connecting said movable member to said take-up means for causing said take-up means to store a portion of said film when said pressure changes from said first level to said second level, said first pressure responsive surface member pressing against said film and urging it toward said breast-supporting surface member when in its first position and being displaced from said film when in its second position, whereby said film is free to advance from said supply means to said take-up means when the pressure in said airtight chamber is changed from said first level to said second level, and said film is pressed substantially against said image forming surface when said pressure is at said first level.

17. Apparatus according to claim 16 further comprising means for determining the second position of said pressure responsive movable member including a member slidably mounted in said housing and means connected to said slidably mounted member for limiting movement of said second pressure responsive movable member away from the first position for said second pressure responsive movable member to a distance which is a function of the position of said slidably mounted member, thereby variably determining said second position, said slidably mounted member having a surface movable in a path leading toward the breast placed on said surface member, to a position adjacent the breast whereby the amount of film advanced from said supply means to said take-up means is a function of the size of the breast.

18. Apparatus according to claim 17 wherein said movement limiting means comprises a surface disposed in the path of movement of said pressure responsive movable member.

19. Apparatus according to claim 17 wherein said slidably mounted member is opaque to X-rays for shielding at least a portion of the film adjacent the area of the screen on which no image of the breast is formed from said source of X-rays.

20. Apparatus according to claim 19 further comprising a fence assembly movably mounted in said housing and having a breast-engaging surface movable with said fence assembly from a position where the breast is prevented by the breast engaging surface from extending beyond the film when the breast is placed on said supporting member, to a position engaging the breast whereat the breast is permitted to extend beyond the film, said fence assembly having further mounted thereon a shield opaque to X-rays and movable from a position within the path of X-rays from said source to the breast to a position out of said path.

21. Apparatus according to claim 20 wherein said shield has a dimension substantially equal to a parallel dimension of the usable area of said film.

* * * * *